(12) United States Patent
Aoyagi et al.

(10) Patent No.: US 9,078,568 B2
(45) Date of Patent: Jul. 14, 2015

(54) MEDICAL IMAGE PROCESSING SYSTEM AND A METHOD FOR PROCESSING A MEDICAL IMAGE

(75) Inventors: Kota Aoyagi, Nasushiobara (JP); Hitoshi Yamagata, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 659 days.

(21) Appl. No.: 12/973,146

(22) Filed: Dec. 20, 2010

(65) Prior Publication Data
US 2011/0166418 A1 Jul. 7, 2011

(30) Foreign Application Priority Data
Jan. 7, 2010 (JP) .................................. 2010-002230

(51) Int. Cl.
| | | |
|---|---|---|
| A61B 1/00 | (2006.01) | |
| A61B 1/04 | (2006.01) | |
| A61B 6/03 | (2006.01) | |
| A61B 6/00 | (2006.01) | |
| G06T 1/00 | (2006.01) | |
| A61B 5/06 | (2006.01) | |

(52) U.S. Cl.
CPC .............. *A61B 6/032* (2013.01); *A61B 1/0005* (2013.01); *A61B 1/00009* (2013.01); *A61B 6/50* (2013.01); *A61B 6/5247* (2013.01); *G06T 1/00* (2013.01); *A61B 1/04* (2013.01); *A61B 5/06* (2013.01)

(58) Field of Classification Search
CPC ........... A61B 2019/505; A61B 1/0005; A61B 2019/5291; A61B 2019/5289; A61B 2019/5297

USPC ................................... 600/109, 114, 117, 118
See application file for complete search history.

(56) References Cited

U.S. PATENT DOCUMENTS

| 2007/0149846 A1* | 6/2007 | Chen et al. ..................... 600/117 |
|---|---|---|
| 2008/0097155 A1* | 4/2008 | Gattani et al. ................. 600/117 |
| 2009/0292175 A1 | 11/2009 | Akimoto et al. |

FOREIGN PATENT DOCUMENTS

| CN | 1612708 A | 5/2005 |
|---|---|---|
| CN | 1678234 A | 10/2005 |
| CN | 100418467 C | 9/2008 |

(Continued)

OTHER PUBLICATIONS

Combined Office Action and Search Report issued Dec. 5, 2012 in Chinese Application No. 201110002617.3 with English translation of categories of cited documents.

*Primary Examiner* — Anhtuan T Nguyen
*Assistant Examiner* — Alexandra Newton
(74) *Attorney, Agent, or Firm* — Oblon, McClelland, Maier & Neustadt, L.L.P.

(57) ABSTRACT

The medical image processing device comprises a detection part, a storage part, an image generation part, and a display-control part. The detection part detects positions and directions of an endoscope. The storage part stores medical image data showing tubular tissues generated by a medical imaging device different from the endoscope. The image generation part generates virtual endoscopic image data showing the internal portion of the tubular tissues based on the medical image data having a position that is a predetermined distance away from the position of the endoscope as a viewpoint. The display-control part receives endoscopic image data showing the internal portion of the tubular tissues generated by the endoscope and displays an endoscopic image based on the endoscopic image data and a virtual endoscopic image based on the virtual endoscopic image data on a display part.

10 Claims, 8 Drawing Sheets

(56) References Cited

FOREIGN PATENT DOCUMENTS

| JP | 9-81787 | 3/1997 |
|---|---|---|
| JP | 2005-21355 | 1/2005 |
| JP | 2009-56238 | 3/2009 |
| JP | 2009-279249 | 12/2009 |
| JP | 2009-279251 | 12/2009 |
| WO | WO 2008/111070 A2 | 9/2008 |

* cited by examiner

ENTRY-OF-BODY-CAVITY SIDE

ENTRY-OF-BODY-CAVITY SIDE

ENTRY-OF-BODY-CAVITY SIDE

MEDICAL IMAGE PROCESSING SYSTEM AND A METHOD FOR PROCESSING A MEDICAL IMAGE

CROSS-REFERENCE TO RELATED APPLICATION

This application is based upon and claims the benefit of priority from Japanese Patent Application No. 2010-002230, filed Jan. 7, 2010; the entire contents of which are incorporated herein by reference

FIELD

The embodiments of the present invention relate to a medical image processing system and a method for processing a medical image, for displaying images obtained by an endoscopic system (hereinafter referred to as "endoscopic images") and medical images obtained by a medical image diagnosis system such as an X-ray CT system.

BACKGROUND

An endoscopic system is a system for observing or treating the internal portion of body cavities by inserting an endoscope comprising an imaging system into body cavities of a subject. An endoscopic system is used for observation and/or treatment of, for example, sites such as the bronchi, the esophagus, or the large intestine.

Additionally, it is possible to generate virtual endoscopic images (hereinafter may be referred to as "virtual endoscopic image") using medical image data obtained by medical image diagnosis systems such as X-ray CT systems and/or MRI systems (magnetic resonance imaging systems). These virtual endoscopic images are used for aiding endoscope operation at the time of examination or treatment using an endoscopic system and have a complementary function of endoscopic images. For example, at the time of examination or treatment using an endoscopic system, an endoscopic image obtained in real time and a virtual endoscopic image are displayed side by side (for example, Japanese published unexamined application No. 2005-21355). In this case, the position of a viewpoint and a view direction are matched on both images to display the endoscopic image and virtual endoscopic image side by side. Furthermore, it is possible to effectively perform observation using the endoscopic image by superimposing and displaying the results through a CAD (Computer Aided Diagnosis) on the virtual endoscopic image.

By displaying the endoscopic image and virtual endoscopic image side by side, it is possible to effectively perform observation using the endoscopic image while advancing an endoscope within a body cavity of a subject. On the other hand, with regard to observation using an endoscopic system, observation may be performed by advancing the endoscope and by retracting the endoscope. This is because observation by advancing the endoscope may cause perforation; therefore, observation by retracting it is safer.

When an endoscopic image and virtual endoscopic image are displayed, the view directions of each image are also matched. When an endoscopic image and virtual endoscopic image are displayed by retracting an endoscope, the view direction of the virtual endoscopic image faces the opposite direction from the traveling direction of the endoscope. The virtual endoscopic image generated according to this view direction does not show an image facing toward the traveling direction of the endoscope. Therefore, there is a problem in which it is impossible to operate the endoscope while confirming the traveling direction of the endoscope using a virtual endoscopic image.

On the other hand, methods for generating and displaying virtual endoscopic images having the opposite direction from the view direction of an endoscopic image as a view direction have been proposed (for example, Japanese published unexamined application No. H 9-81787). In this case, a field of vision such as a rearview mirror can be obtained. However, since the view directions are opposite direction between the endoscopic image and virtual endoscopic image, it is not easy to intuitively understand a correspondence relationship with the endoscopic image on the virtual endoscopic image.

Moreover, even in the case of advancing an endoscope within the body cavities of a subject, a viewpoint of the virtual endoscopic image is set to the tip position of the endoscope. Therefore, it is impossible to fully assure a field of vision of the traveling direction of the endoscope on the virtual endoscopic images generated according to that viewpoint, and this may cause perforation.

DETAILED DESCRIPTION

Constitution

First Embodiment

Figure 1:
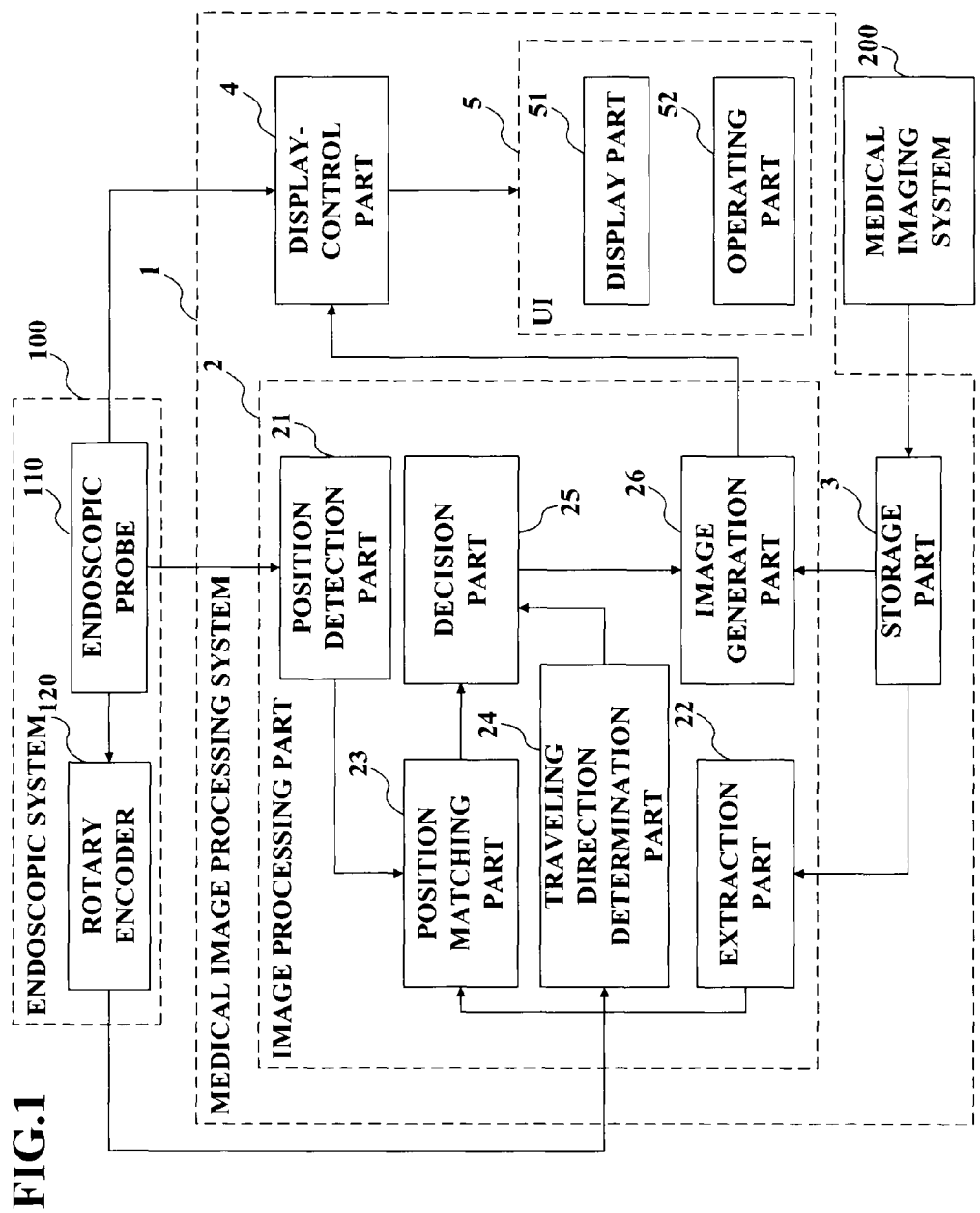
FIG. 1 is a block diagram showing a medical image processing system according to the first embodiment.

With reference to FIG. 1, the medical image processing system according to the first embodiment is described. The medical image processing system 1 according to the first embodiment is connected to an endoscopic system 100 and a medical imaging system 200. As the medical imaging system 200, imaging systems, for example, X-ray CT systems, MRI systems (magnetic resonance imaging system), etc., are used. The medical image processing system 1 receives endoscopic image data from the endoscopic system 100 and receives medical image data different from the endoscopic image data from the medical imaging system 200.

(Endoscopic System 100)

The endoscopic system 100 comprises an endoscopic probe 110. As the endoscopic probe 110, known endoscopic probes having a CCD camera (charge-coupled system camera) and optical fiber as an imaging part are used. For example, the endoscopic probe 110 has a cable-like shape and an imaging part is provided at the tip. The endoscopic probe 110 generates endoscopic image data showing the internal portion of a subject by imaging while a tip portion (imaging part) is inserted in the subject. For example, the imaging subjects are assumed to be tubular tissues such as the large intestine, bronchi, or esophagus. Hereinafter, a case in which an imaging subject is the large intestine is described; however, the same action and effect can be achieved when the imaging subject is tubular tissues other than the large intestine.

The endoscopic probe 110 generates endoscopic image data showing the internal portion of the large intestine by imaging while a tip portion (imaging part) is inserted into the large intestine. For example, an operator inserts the tip portion (imaging part) of the endoscopic probe 110 into the large intestine and advances the tip portion along the large intestine to perform imaging. Alternatively, an operator performs imaging by retracting the endoscopic probe 110 along the large intestine. The endoscopic system 100 generates endoscopic image data at each position in the tubular tissue and outputs the endoscopic image data at each position to the medical image processing system 1. The endoscopic probe 110 corresponds to an example of the "endoscope".

Furthermore, the endoscopic system 100 comprises a rotary encoder 120 as an example. The rotary encoder 120 is an example of means for determining the traveling direction of the endoscopic probe 110. As the rotary encoder 120, known rotary encoders can be used. As the rotary encoder 120, for example, incremental type or absolute type rotary encoders can be used.

The rotary encoder 120 generates pulses whenever the endoscopic probe 110 is advanced by a fixed distance. Similarly, the rotary encoder 120 generates pulses whenever the endoscopic probe 110 is retracted by a fixed distance. By counting the number of pulses generated by the rotary encoder 120, the amount of travel of the endoscopic probe 110 can be detected. For example, the rotary encoder 120 outputs A phase pulses and B phase pulses in accordance with the rotation of the axis of the encoder. The rotary encoder 120 is configured so as to output two pulses (A phase pulse and B phase pulse) by shifting the timing (phase). Moreover, the output timing is made into an opposite relationship by the rotation direction of the axis of the rotary encoder 120. For example, when the endoscopic probe 110 is advanced, A phase pulses are output first from the rotary encoder 120, and in the meantime B phase pulses are output from the rotary encoder 120. On the other hand, when the endoscopic probe 110 is retracted, B phase pulses are output first from the rotary encoder 120, and in the meantime A phase pulses are output from the rotary encoder 120. That is, it is possible to identify the rotation direction and the amount of rotation of the axis of the rotary encoder 120 using a relationship between two types of pulses. From this, the traveling direction (advance or retraction) of the endoscopic probe 110 can be determined.

The signals generated by the rotary encoder 120 are output to the traveling direction determination part 24 of the image processing part 2.

(Medical Imaging System 200)

As the medical imaging system 200, imaging systems such as X-ray CT systems and/or MRI systems are used. In this embodiment, the medical imaging system 200, by imaging a 3-dimensional imaging region, generates volume data showing the 3-dimensional imaging region as medical image data. When an X-ray CT system is used as the medical imaging system 200, by imaging a 3-dimensional imaging region, CT image data at a plurality of cross-sections each having different cross-section positions is generated and volume data showing the 3-dimensional imaging region is generated. When the imaging subject is the large intestine, the X-ray CT system images a 3-dimensional imaging region including the large intestine; thereby, it generates volume data showing the large intestine. The medical imaging system 200 outputs the volume data to the medical image processing system 1.

For example, before the endoscopic system 100 is used to examine or treat the large intestine, imaging of the large intestine is performed using the medical imaging system 200. After imaging using the medical imaging system 200, the internal portion of the large intestine is imaged by the endoscopic system 100; thereby, endoscopic image data showing the internal portion of the large intestine is generated.

(Medical Image Processing System 1)

The medical image processing system 1 comprises an image processing part 2, a storage part 3, a display-control part 4, and a user interface (UI) 5. The storage part 3 stores medical image data generated by the medical imaging system 200. As an example, the storage part 3 stores volume data showing the large intestine. The storage part 3 corresponds to an example of the "storage part".

(Image Processing Part 2)

The image processing part 2 comprises a position detection part 21, an extraction part 22, a position matching part 23, a traveling direction determination part 24, a decision part 25, and an image generation part 26.

(Position Detection Part 21)

The position detection part 21 detects the position and orientation (direction) of the endoscopic probe 110. As an example, the position detection part 21 uses magnetism to detect the position and orientation of the endoscopic probe 110. For example, a magnetism generation part and magnetism detection part, which are not shown in the Figures, are used. The magnetism generation part is placed at an arbitrary position and generates magnetism. The magnetism detection part is mounted and fixed in the vicinity of the endoscopic probe 110.

The magnetism detector detects magnetism from the magnetism generation part and generates current depending on the strength of the detected magnetism. The position detection part 21 detects the current from the magnetism detection part and outputs the position information and direction information in 3-dimensional space regarding the magnetism detection part for the magnetism generation part to the position matching part 23. In this way, the position of the tip and the orientation of the tip of the endoscopic probe 110 are detected having the position of the magnetism generation part as the origin. The position detection part 21 corresponds to an example of the "detection part".

(Extraction Part 22)

The extraction part 22 reads volume data from the storage part 3 and extracts volume data showing the site of the imaging subject from the volume data. The extraction part 22 extracts volume data showing the site of the imaging subject from the volume data based on, for example, pixel values. As an example, when the imaging subject is the large intestine, the extraction part 22 extracts volume data showing the large intestine from the volume data based on the pixel values. The extraction part 22 outputs the volume data showing the site of the imaging subject to the position matching part 23.
(Position Matching Part 23)

The position matching part 23 receives the position information indicating the position of the tip and the direction information indicating the orientation of the tip of the endoscopic probe 110 from the position detection part 21. Furthermore, the position matching part 23 receives the volume data showing the site of the imaging subject (for example, the large intestine) from the extraction part 22. The position matching part 23 identifies the position and direction of the tip of the endoscopic probe 110 on the volume data showing the large intestine.

For example, the position matching part 23, by matching the trajectory of the position of the tip of the endoscopic probe 110 in 3-dimensional space and the volume data showing the large intestine obtained by the extraction part 22 through a pattern matching, identifies the position of the tip and the orientation of the tip of the endoscopic probe 110 on the volume data. Specifically, the position matching part 23, by matching the trajectory of the position of the magnetism detection part that is output from the position detection part 21 and the volume data showing the large intestine through the pattern matching, identifies the position of the tip and the orientation of the tip of the endoscopic probe 110 on the volume data.

Alternatively, an operator may specify the position and orientation of the tip of the endoscopic probe 110 using an operating part 52. In this case, the image generation part 26 generates 3-dimensional image data showing the large intestine based on the volume data showing the large intestine. The display-control part 4 displays the 3-dimensional image showing the large intestine on a display part 51. An operator uses the operating part 52 to specify the position of the tip and the orientation of the tip of the endoscopic probe 110 for the 3-dimensional image showing the large intestine. The position information indicating the position and the direction information indicating the orientation specified by the operating part 52 are output to the position matching part 23. The position matching part 23 defines the position and orientation specified by the operating part 52 as the position and orientation of the tip of the endoscopic probe 110 on the volume data.

Alternatively, the position matching part 23 may specify the position of the tip and the orientation of the tip of the endoscopic probe 110 on the volume data by matching positions using the feature points of the site of the observation subject (for example, the large intestine). For example, the position matching part 23 extracts the feature points of the large intestine from the volume data showing the site of the observation subject (for example, the large intestine).

Additionally, the position matching part 23 extracts the feature points of the large intestine from the trajectory of the position of the tip of the endoscopic probe 110 in 3-dimensional space. Subsequently, the position matching part 23, by matching the positions of the feature points, identifies the position of the tip and the orientation of the tip of the endoscopic probe 110 on the volume data.

The position matching part 23 outputs the position information indicating the position of the tip and the direction information indicating the orientation of the tip of the endoscopic probe 110 on the volume data showing the large intestine to the decision part 25.

(Traveling Direction Determination Part 24)

The traveling direction determination part 24 receives the abovementioned signals (as an example, two types of pulse signals) from the rotary encoder 120 of the endoscopic system 100 to determine the traveling direction of the endoscopic probe 110. That is, the traveling direction determination part 24 determines whether the endoscopic probe 110 is advancing or retracting. In other words, the traveling direction determination part 24 determines whether the endoscopic probe 110 is traveling forward or traveling backward. The traveling direction determination part 24 outputs the information indicating the traveling direction of the endoscopic probe 110 to the decision part 25. Specifically, the traveling direction determination part 24 outputs the advancing information indicating that the endoscopic probe 110 is traveling forward or the retracting information indicating that the endoscopic probe 110 is traveling backward to the decision part 25. Determination process by the traveling direction determination part 24 may be performed by the rotary encoder 120.
(Decision Part 25)

The decision part 25 decides the position of the viewpoint and the view direction used for image generation processing at the image generation part 26. Specifically, the decision part 25 receives the position information indicating the position of the tip and the direction information indicating the orientation of the tip of the endoscopic probe 110 on the volume data showing the large intestine from the position matching part 23. Additionally, the decision part 25 receives the information indicating the traveling direction (advancing or retracting) of the endoscopic probe 110 from the traveling direction determination part 24. Subsequently, the decision part 25 decides the position of the viewpoint and the view direction used for image generation processing based on the position of the tip, the orientation of the tip, and the traveling direction of the endoscopic probe 110.

The decision part 25 sets the position that is a predetermined distance away in the traveling direction from the position of the tip of the endoscopic probe 110 as the position of the viewpoint used for image generation processing. Additionally, the decision part 25 sets the orientation of the tip of the endoscopic probe 110 as the view direction used for image generation processing. That is, the decision part 25 sets the view direction used for image generation processing to the same as the orientation of the tip of the endoscopic probe 110. The decision part 25 outputs the viewpoint position information (coordinate information) indicating the position of the viewpoint and the view direction information indicating the view direction used for image generation processing to the image generation part 26. The predetermined distance described above may be decided in advance or may be decided by an operator arbitrarily. For example, when an operator inputs the value of the predetermined distance using the operating part 52, the information indicating the predetermined distance is output from the user interface (UI) 5 to the decision part 25.

The predetermined distance may be a different value depending on the site of the observation subject, or the same value. For example, it is preferred to determine the predetermined distance such that, when compared to endoscopic images, a position easily observed using virtual endoscopic images is set to the position of the viewpoint. As an example, it is preferred that the predetermined distance is approximately 5 mm; however, the predetermined distance may be changed depending on the site of the observation subject and/or the position of the viewpoint. For example, the predetermined distance may be set relatively long at a part in which the tubular tissue is straight, and the predetermined distance may be set relatively short at a part in which the tubular tissue is curved.

(Image Generation Part 26)

The image generation part 26 reads the volume data from the storage part 3. Additionally, the image generation part 26 receives the viewpoint position information and the view direction information from the decision part 25. The image generation part 26 performs volume rendering from the position of the viewpoint indicated by the viewpoint position information toward the view direction indicated by the view direction information to generate virtual endoscopic image data showing the internal portion of the tubular tissue such as the large intestine. The image generation part 26 outputs the virtual endoscopic image data to the display-control part 4. The image generation part 26 corresponds to an example of the "image generation part".

(Display-Control Part 4)

The display-control part 4 receives the virtual endoscopic image data from the image generation part 26 and displays the virtual endoscopic image based on the virtual endoscopic image data on the display part 51. Additionally, the display-control part 4 receives the endoscopic image data from the endoscopic system 100 and displays the endoscopic image based on the endoscopic image data on the display part 51. For example, the display-control part 4 displays the endoscopic image and virtual endoscopic image side by side on the display part 51. Alternatively, the display-control part 4 may superimpose and display the endoscopic image and virtual endoscopic image on the display part 51. The display-control part 4 corresponds to an example of the "display-control part".

(User Interface (UI) 5)

The user interface (UI) 5 comprises the display part 51 and the operating part 52. The display part 51 is composed of a monitor such as a CRT (cathode ray tube) and liquid crystal display. The operating part 52 is composed of an input system such as keyboard and mouse.

The image processing part 2 and the display-control part 4 may composed of a processing system, which is not shown in the Figures, such as CPU (central processing unit), GPU (graphics processing unit), or ASIC (application specific integrated circuit), and a storage system, which is not shown in the Figures, such as ROM (read only memory), RAM (random access memory), or HDD (hard disk drive), respectively.

In the storage system, the image processing program for executing the functions of the image processing part 2 and the display-control program for executing the functions of the display-control part 4 are stored. Additionally, the image processing program includes the position detection program for executing the function of the position detection part 21, the extraction program for executing the function of the extraction part 22, the position matching program for executing the function of the position matching part 23, the traveling direction determination program for executing the function of the traveling direction determination part 24, the decision program for executing the function of the decision part 25, and the image generation program for executing the function of the image generation part 26. Moreover, the processing system such as CPU executes each program stored in a storage system; thereby, the functions of each part are executed.

The image processing program and display-control program configures an example of the "medical image processing program".

(Operation)

Subsequently, the operations of the medical image processing system 1 according to the first embodiment are described separately for the case in which the endoscopic probe 110 is advancing and for the case in which it is retracting.

(The Case in which the Endoscopic Probe 110 is Advancing)

Figure 2A:
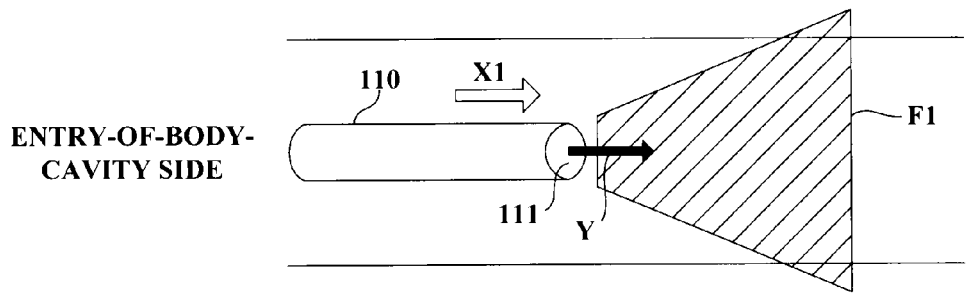
FIG. 2A is a diagram showing the position of a viewpoint in the case in which an endoscopic probe is advancing.
Figure 2B:
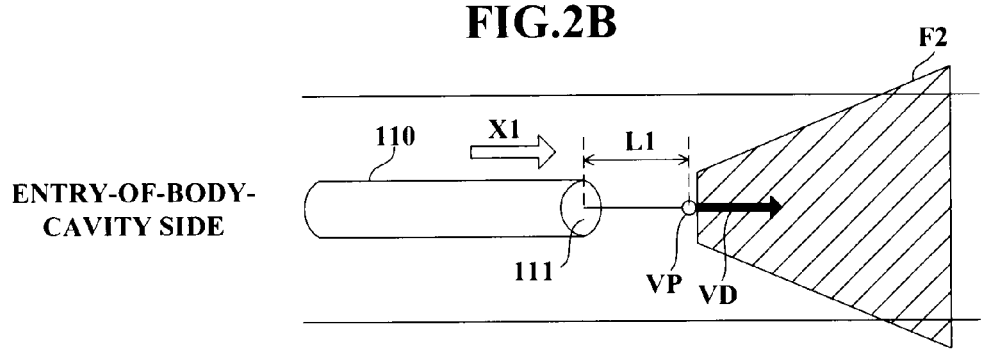
FIG. 2B is a diagram showing the position of a viewpoint in the case in which an endoscopic probe is advancing.
Figure 2C:
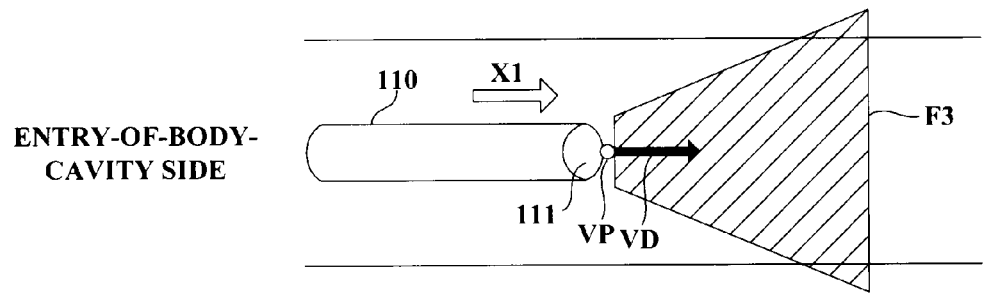
FIG. 2C is a diagram showing the position of a viewpoint in the case in which an endoscopic probe is advancing.

With reference to FIG. 2A to FIG. 2C, an example for setting the viewpoint position in the case in which the endoscopic probe 110 is advancing is described. Additionally, FIG. 3A to FIG. 3C show an example of images displayed on the display part 51.

As shown in FIG. 2A, as an example, the case in which the endoscopic probe 110 is advancing in the large intestine in the arrow X1 direction is described. The endoscopic probe 110, by performing imaging inside the view F1, generates the endoscopic image data in the view F1 in real time. The display-control part 4 receives the endoscopic image data in the view F1 from the endoscopic system 100 and displays the endoscopic image in the view F1 on the display part 51 in real time.

Figure 3A:
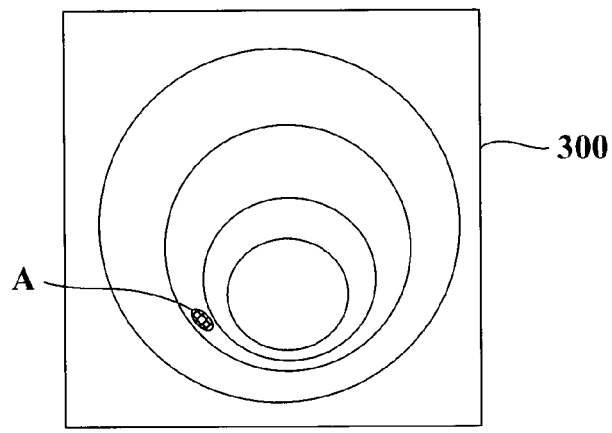
FIG. 3A is a diagram showing an endoscopic image in the case in which an endoscopic probe is advancing.
Figure 3B:
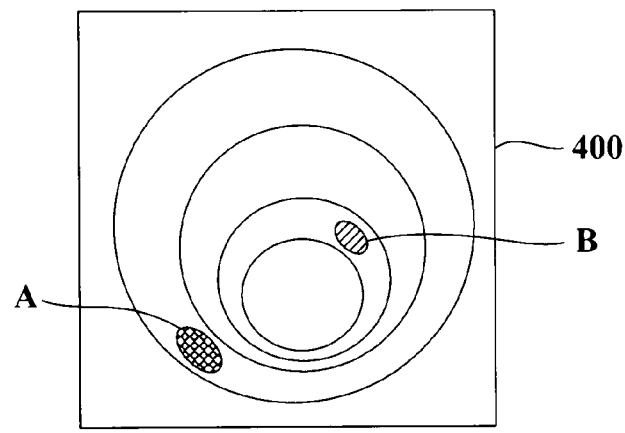
FIG. 3B is a diagram showing a virtual endoscopic image in the case in which an endoscopic probe is advancing.
Figure 3C:
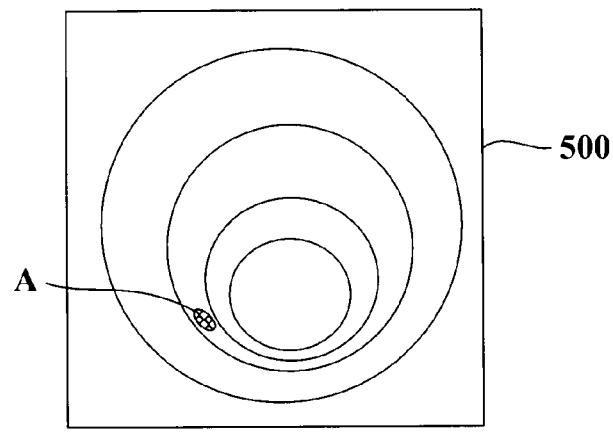
FIG. 3C is a diagram showing a virtual endoscopic image in the case in which an endoscopic probe is advancing.

FIG. 3A shows a display example of the endoscopic image. As shown in FIG. 3A, the endoscopic image 300 in the view F1 is displayed on the display part 51. The tumor candidate A is shown in the endoscopic image 300. By performing imaging while advancing the endoscopic probe 110, the endoscopic image 300 at each position is displayed on the display part 51 in real time.

The position detection part 21 detects the position of the tip portion 111 of the endoscopic probe 110 and the direction (orientation) to which the tip portion 111 is facing. In the example shown in FIG. 2A, the arrow Y direction corresponds to the orientation of the tip portion 111. Moreover, the traveling direction determination part 24 determines the traveling direction of the endoscopic probe 110 based on the signal from the rotary encoder 120. In the example shown in FIG. 2A, since the endoscopic probe 110 is advancing in the arrow X1 direction, the traveling direction determination part 24 determines that the endoscopic probe 110 is traveling in the forward direction (arrow X1 direction).

The decision part 25 decides the position of the viewpoint and the view direction used for image generation processing based on the position of the tip portion 111, the orientation (arrow Y direction) of the tip portion 111 of the endoscopic probe 110, and the traveling direction (forward direction) of the endoscopic probe 110. For example, as shown in FIG. 2B, the decision part 25 sets the position that is a predetermined distance (for example, distance L1) away from the position of the tip portion 111 of the endoscopic probe 110 in the forward direction (arrow X1 direction) as the position of the viewpoint VP used for image generation processing. The distance L1 is a value preset to the decision part 25, and it can be changed by an operator arbitrarily using the operating part 52. For example, assume that the distance L1 is approximately 5 cm. Additionally, the decision part 25 sets the direction (arrow Y direction) of the tip portion 111 of the endoscopic probe 110 as the view direction VD used for image generation processing. In other words, the same direction as the direction (arrow Y direction) to which the tip portion 111 of the endoscopic probe 110 is facing is set as the view direction VD. The position detection part 21, traveling direction determination part 24, and decision part 25 perform processing in real time respectively; thereby, the position of the viewpoint and the view direction used for image generation processing are decided in real time.

Moreover, the image generation part 26, by performing volume rendering from the position of the viewpoint VP to the view direction VD, the virtual endoscopic image data showing the internal portion of the large intestine is generated. In the example shown in FIG. 2B, the region from the viewpoint VP facing the view direction VD is the view F2, and the image generation part 26 generates the virtual endoscopic image data in the view F2. The display-control part 4 receives the virtual endoscopic image data in the view F2 from the image generation part 26 and displays the virtual endoscopic image in the view F2 on the display part 51.

FIG. 3B shows a display example of the virtual endoscopic image. As shown in FIG. 3B, the virtual endoscopic image 400 in the view F2 is displayed on the display part 51. The tumor candidate A and tumor candidate B are shown in the virtual endoscopic image 400.

As shown in FIG. 2C, when the position of the tip portion 111 of the endoscopic probe 110 is the position of the viewpoint VP, the region from the viewpoint VP facing the view direction VD is the view F3 and the virtual endoscopic image data in the view F3 are generated.

FIG. 3C shows a display example of this virtual endoscopic image. As shown in FIG. 3C, the virtual endoscopic image 500 in the view F3 is displayed on the display part 51. The tumor candidate A is shown in the virtual endoscopic image 500. Since the viewpoint VP has been set to the position of the tip portion 111 of the endoscopic probe 110, the view F3 and the view F1 are the same region. Therefore, the same region is shown on the endoscopic image 300 and the virtual endoscopic image 500.

As an example, the display-control part 4 displays the endoscopic image 300 and the virtual endoscopic image 400 side by side on the display part 51. The display-control part 4 updates the endoscopic image 300 and the virtual endoscopic image 400 in real time to displays on the display part 51.

As above, when the endoscopic probe 110 is advanced forward, if the position at the distance L1 in the forward direction away from the tip portion 111 of the endoscopic probe 110 is the position of the viewpoint VP and the orientation of the tip portion 111 is set to the view direction VD, it is possible to assure the view F2 forward from the view F1 of the endoscopic probe 110. This makes it possible to generate and display the virtual endoscopic image 400 showing the tumor candidate B included in the view F2 forward from the view F1.

In other words, when the endoscopic probe 110 is advanced forward, if the virtual endoscopic image 400 in the view F2 forward from the tip portion 111 of the endoscopic probe 110 is generated and displayed, an operator can confirm the region forward from the endoscopic image 300 in advance while operating the endoscopic probe 110. As a result, it is possible to improve efficiency of examination using the endoscopic system 100, and moreover, it is possible to improve safety in operation of the endoscopic probe 110.

(The Case in which the Endoscopic Probe 110 is Retracting)

Figure 4A:
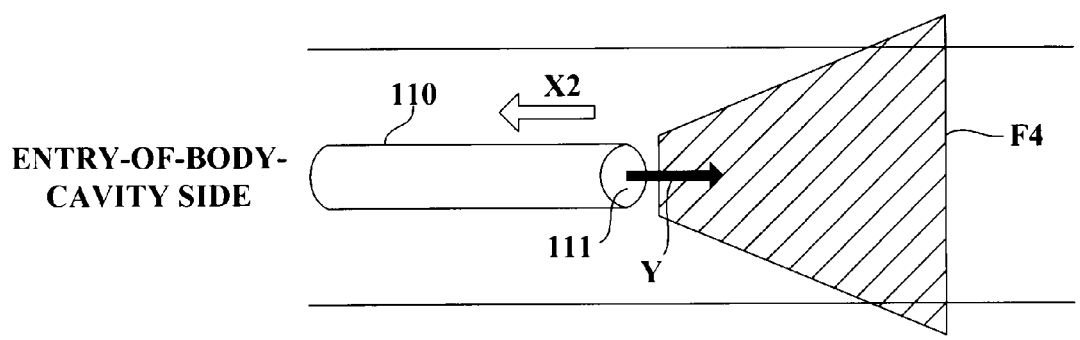
FIG. 4A is a diagram showing the position of a viewpoint in the case in which an endoscopic probe is retracting.
Figure 4B:
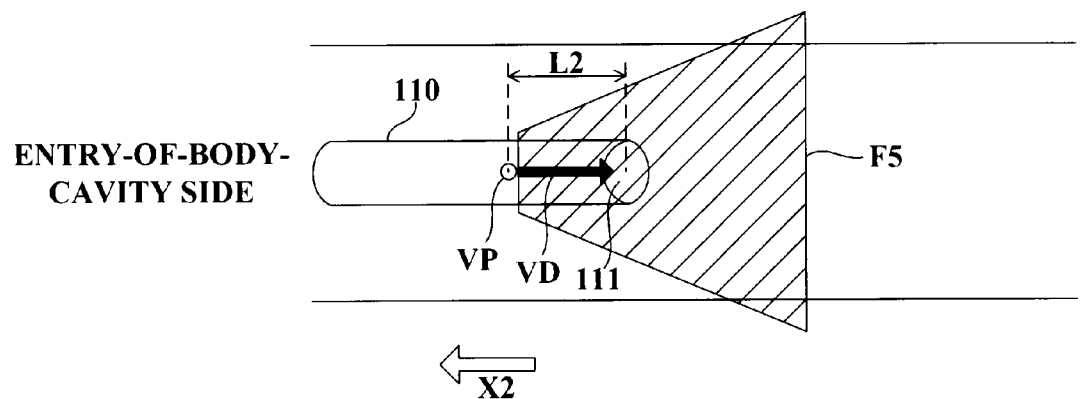
FIG. 4B is a diagram showing the position of a viewpoint in the case in which an endoscopic probe is retracting.

With reference to FIG. 4A and FIG. 4B, an example for setting the viewpoint position in the case in which the endoscopic probe 110 is retracting. Additionally, FIG. 5A and FIG. 5B show an example of images displayed on the display part 51.

As an example, as shown in FIG. 4A, the case in which the endoscopic probe 110 is retracting in the large intestine in the arrow X2 direction is described. The endoscopic probe 110, by performing imaging inside the view F4, generates the endoscopic image data in the view F4 in real time. The display-control part 4 receives the endoscopic image data in the view F4 from the endoscopic system 100 and displays the endoscopic image in the view F4 on the display part 51 in real time.

Figure 5A:
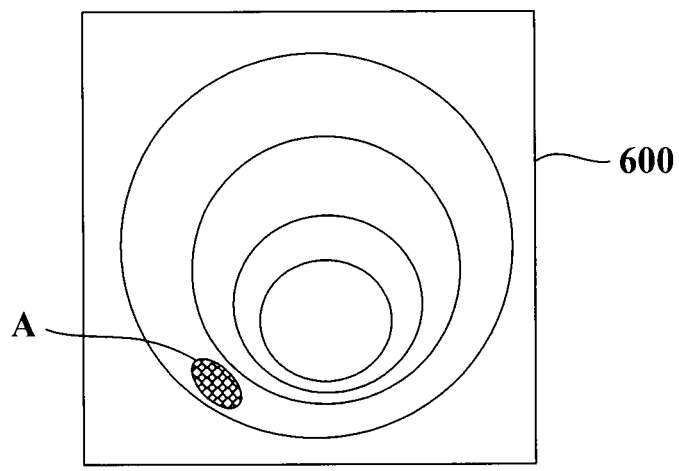
FIG. 5A is a diagram showing an endoscopic image in the case in which an endoscopic probe is retracting.
Figure 5B:
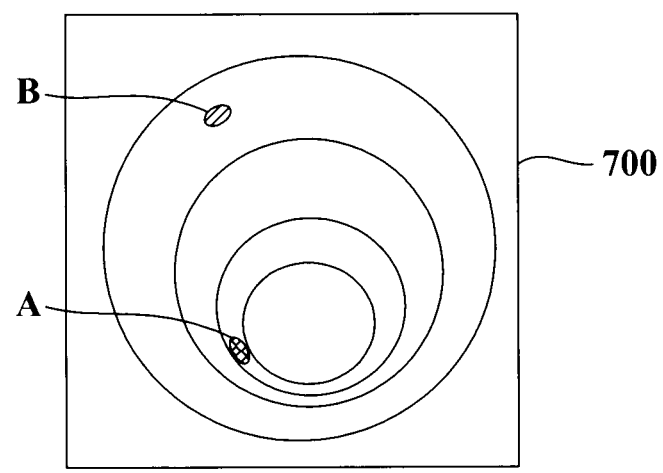
FIG. 5B is a diagram showing a virtual endoscopic image in the case in which an endoscopic probe is retracting.

FIG. 5A shows a display example of the endoscopic image. As shown in FIG. 5A, the endoscopic image 600 in the view F4 is displayed on the display part 51. The tumor candidate A is displayed in the endoscopic image 600. By performing imaging while retracting the endoscopic probe 110, the endoscopic image 600 at each position is displayed on the display part 51 in real time.

The position detection part 21 detects the position of the tip portion 111 of the endoscopic probe 110 and the direction (orientation) to which the tip portion 111 is facing. In the example shown in FIG. 4A, the arrow Y direction corresponds to the orientation of the tip portion 111. Moreover, the traveling direction determination part 24 determines the traveling direction of the endoscopic probe 110 based on the signal from the rotary encoder 120. In the example shown in FIG. 4A, since the endoscopic probe 110 is retracting in the arrow X2 direction, the traveling direction determination part 24 determines that the endoscopic probe 110 is traveling in the backward direction (arrow X2 direction).

The decision part 25 decides the position of the viewpoint and the view direction used for image generation processing based on the position of the tip portion 111, the direction (arrow Y direction) of the tip portion 111 of the endoscopic probe 110, and the traveling direction (backward direction) of the endoscopic probe 110. For example, as shown in FIG. 4B, the decision part 25 sets the position that is a predetermined distance (for example, distance L2) away from the position of the tip portion 111 of the endoscopic probe 110 in the backward direction (arrow X2 direction) as the position of the viewpoint VP used for image generation processing. The distance L2 is a value preset to the decision part 25, and it can be changed by an operator arbitrarily using the operating part 52. For example, the distance L2 is approximately 5 cm. Additionally, the decision part 25 sets the direction (arrow Y direction) of the tip portion 111 of the endoscopic probe 110 as the view direction VD used for image generation processing. In other words, it sets the same direction as the direction (arrow Y direction) to which the tip portion 111 of the endoscopic probe 110 is facing as the view direction VD. The position detection part 21, the traveling direction determination part 24, and the decision part 25 perform processing in real time respectively; thereby, the position of the viewpoint and the view direction used for image generation processing are decided in real time.

Moreover, the image generation part 26 performs volume rendering from the position of the viewpoint VP toward the view direction VD; thereby, the virtual endoscopic image data showing the internal portion of the large intestine is generated. In the example shown in FIG. 4B, the region from the viewpoint VP facing the view direction VD is the view F5, and the image generation part 26 generates the virtual endoscopic image data in the view F5. The display-control part 4 receives the virtual endoscopic image data in the view F5 from the image generation part 26 and displays the virtual endoscopic image in the view F5 on the display part 51.

FIG. 5B shows a display example of the virtual endoscopic image. As shown in FIG. 5B, the virtual endoscopic image 700 in the view F5 is displayed on the display part 51. The tumor candidate A and tumor candidate B are shown in the virtual endoscopic image 700.

As an example, the display-control part 4 displays the endoscopic image 600 and the virtual endoscopic image 700 side by side on the display part 51. The display-control part 4 updates the endoscopic image 600 and the virtual endoscopic image 700 in real time and displays on the display part 51.

As above, when the endoscopic probe 110 is traveled backward, if the position away from the tip portion 111 of the endoscopic probe 110 at the distance L2 in the backward direction is the position of the viewpoint VP and the orientation of the tip portion 111 is the view direction VD, it is possible to assure the view F5 backward from the view F4 of the endoscopic probe 110. This makes it possible to generate and display the virtual endoscopic image 700 showing the tumor candidate B included in the view F5 backward from the view F4.

In other words, when the endoscopic probe 110 is traveled backward (pulled back), the virtual endoscopic image 700 in the view F5 backward from the tip portion 111 of the endoscopic probe 110 is generated and displayed, an operator can confirm the region backward from the endoscopic image 600 in advance and operate the endoscopic probe 110. As a result, it is possible to improve the efficiency of examination using the endoscopic system 100, and also it is possible to improve safety in operation of the endoscopic probe 110.

In this embodiment, the direction (arrow Y direction) of the tip portion 111 of the endoscopic probe 110 is used as the view direction VD; therefore, even when the direction of the tip portion 111 is facing opposite from the traveling direction (arrow X2 direction) of the endoscopic probe 110, the endoscopic image 600 and virtual endoscopic image 700 facing in the same direction can be obtained. In other words, with the endoscopic image 600 and virtual endoscopic image 700, the image having the same view direction can be obtained.

In this way, since the endoscopic image 600 and virtual endoscopic image 700 facing the same direction can be obtained, an operator can understand the position relationship between the endoscopic image 600 and virtual endoscopic image 700 intuitively.

As above, in this embodiment, even when the endoscopic probe 110 is advanced forward or traveled backward, if the position that is a predetermined distance away from the position of the tip of the endoscopic probe 110 in the traveling direction as the position of the viewpoint, it is possible to generate virtual endoscopic images, which correspond to endoscopic images and which show the view of the traveling direction of the endoscopic probe 110, in a manner that is intuitively and easily understood for an operator.

In addition, an operator may change arbitrarily the predetermined distance depending on the position of the viewpoint using the operating part 52 with reference to endoscopic images, virtual endoscopic images, or 3-dimensional images. For example, at a part in which the tubular tissue is straight, an operator may input a value of relatively long distance using the operating part 52 and, at a part in which the tubular tissue is curved, an operator may input a value of relatively short distance using the operating part 52. The value of distance input by the operating part 52 is output to the decision part 25. The decision part 25 decides the position of the viewpoint with the distance input by the operating part 52 as the predetermined distance described above. At a part in which the tubular tissue is straight, it is possible to observe the position further away from the viewpoint of the endoscopic image in advance by making the predetermined distance relatively long. On the other hand, at a section in which the tubular tissue is curved, if the predetermined distance is made relatively long, the viewpoint may be set outside the tubular tissue. In this case, it is possible to set the viewpoint of the virtual endoscopic image in the tubular tissue by making the predetermined distance relatively short at the discretion of an operator.

In the embodiments above, the medical image processing system 1 in which the viewpoint of the virtual endoscopic image is changed by an operator using the operating part 52 is described. However, the medical image processing system 1 is not limited to this, and it may be the system in which the viewpoint of the virtual endoscopic image is changed automatically.

Hereinafter, the configuration of the medical image processing system 1 in which the viewpoint of the virtual endoscopic image is changed automatically is described.

As an example of the condition when switching the viewpoint of the virtual endoscopic image automatically, the status of the endoscopic probe 110 including the traveling direction and traveling speed of the endoscopic probe 110 is used.

The traveling direction determination part 24 receives signals from the rotary encoder 120 to determine the traveling direction and traveling speed of the endoscopic probe 110. Based on the determined traveling direction and traveling speed, the decision part 25 decides the position of the viewpoint of the virtual endoscopic image. Here, a table in which the traveling direction and traveling speed corresponds to the position of the viewpoint of the virtual endoscopic image may be provided.

The display-control part 4 switches automatically, depending on the traveling direction and traveling speed of the endoscopic probe 110, the virtual endoscopic image (shown in FIG. 2C) based on the virtual endoscopic image data generated by the image generation part 26 having the position of the tip of the endoscopic probe 110 as a viewpoint and the virtual endoscopic image (shown in FIG. 2B and FIG. 4B) based on the virtual endoscopic image data generated by image generation part 26 having a position that is the predetermined distance (L1 and L2) away from the position of the tip of the endoscopic probe 110 in the traveling direction as a viewpoint to display on display part 51.

Subsequently, the operation by the medical image processing system 1 is described. For example, when the endoscopic probe 110 is in the rest state (including slight motion), the decision part 25 decides the position of the viewpoint of the virtual endoscopic image (shown in FIG. 2C). When the endoscopic probe 110 is in the advancing state (excluding slight motion), the decision part 25 decides the position of the viewpoint of the virtual endoscopic image (shown in FIG. 2B).

When the endoscopic probe 110 is in the retraction state (excluding slight motion), the decision part 25 decides the position of the viewpoint of the virtual endoscopic image (shown in FIG. 4B).

In the medical image processing system 1 above, since the viewpoint of the virtual endoscopic image is changed automatically, an operator can obtain virtual endoscopic images in accordance with the state of the endoscopic probe 110, it is possible to further improve the efficiency of examination using the endoscopic system 100, and moreover, it is possible to further improve safety in operation of the endoscopic probe 110.

Second Embodiment

Figure 6:
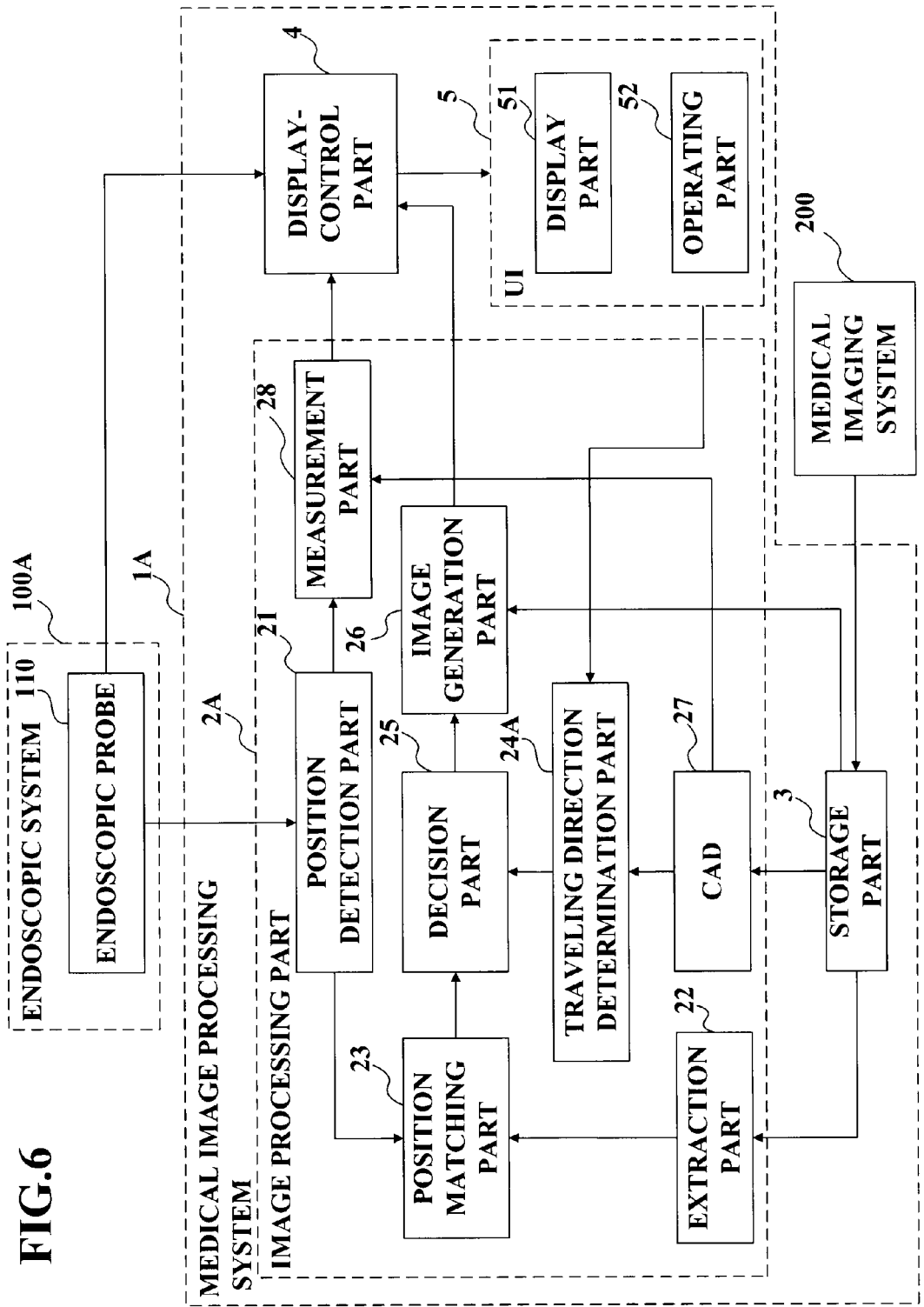
FIG. 6 is a block diagram showing a medical image processing system according to the second embodiment.

With reference to FIG. 6, the medical image processing system according to the second embodiment is described. The medical image processing system 1A according to the second embodiment determines the traveling direction of the endoscopic probe 110 based on the results from CAD (Computer Aided Diagnosis). In the second embodiment, the configuration having the same symbols as in the first embodiment have the same function; therefore, the explanation may be omitted. The medical image processing system 1A according to the second embodiment is connected to the endoscopic system 100A and the medical imaging system 200.

The endoscopic system 100A comprises the endoscopic probe 110. Since the medical image processing system 1A according to the second embodiment determines the traveling direction of the endoscopic probe 110 based on the results from the CAD, the endoscopic system 100A does not comprise the rotary encoder 120.

(Medical Image Processing System 1A)

The medical image processing system 1A comprises an image processing part 2A, the storage part 3, the display-control part 4, and the user interface (UI) 5. The medical image processing system 1A according to the second embodiment comprises the image processing part 2A instead of the image processing part 2 according to the first embodiment.

(Image Processing Part 2A)

The image processing part 2A comprises the position detection part 21, the extraction part 22, the position matching part 23, a traveling direction determination part 24A, the decision part 25, the image generation part 26, the CAD (Computer Aided Diagnosis) 27, and the measurement part 28.

Since the position detection part 21, the extraction part 22, and the position matching part 23 have the same function as the first embodiment, the description thereof is omitted.

(CAD 27)

The CAD (Computer Aided Diagnosis) 27 reads volume data from the storage part 3 and detects the characteristics and/or sites of diseases based on the volume data. When the imaging subject is the large intestine, the CAD 27 identifies the shape and position of the tumor candidate based on the volume data showing the large intestine.

For example, the CAD 27 identifies a protrusion portion based on the curvature of the profile of the large intestine and determines the protrusion portion as a tumor candidate. The CAD 27 outputs the position information indicating the position of the tumor candidate to the display-control part 4, the traveling direction determination part 24A, and the measurement part 28. The CAD 27 corresponds to an example of the "identification part". Additionally, the traveling direction determination part 24A corresponds to an example of the "determination part".

For example, the image generation part 26, by reading volume data from the storage part 3 and by performing volume rendering on the volume data, generates 3-dimensional image data sterically showing the large intestine. The image generation part 26 outputs the 3-dimensional image data sterically showing the large intestine to the display-control part 4. The display-control part 4 superimposes the tumor candidate identified by the CAD 27 on the 3-dimensional image sterically showing the large intestine to display on the display part 51.

An operator refers to the tumor candidate displayed on the display part 51 and uses the operating part 52 to specify a tumor candidate as an observation subject and to specify an observation sequence further.

Figure 7:
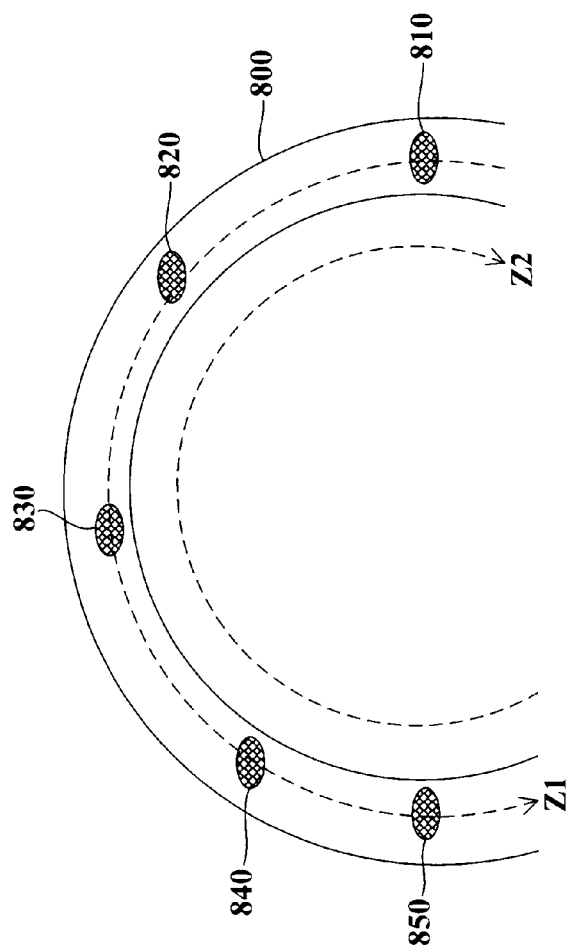
FIG. 7 is a diagram showing tumor candidates that are specified by CAD (Computer Aided Diagnosis).

With reference to FIG. 7, a method for specifying a tumor candidate is described. For example, the 3-dimensional image 800 sterically showing the large intestine is displayed on the display part 51. Furthermore, the tumor candidates 810, 820, 830, 840, and 850 are superimposed on the 3-dimentional image 800. An operator uses the operating part 52 to specify a tumor candidate as an observation subject. As an example, an operator uses the operating part 52 to specify the tumor candidates 810, 820, 830, 840, and 850 in that sequence. For example, the specified sequence corresponds to an observation sequence. In this way, when a tumor candidate and sequence using the operating part 52 are specified, information (coordinate information) indicating the position of the specified tumor candidate and the information indicating the specified sequence are output from the user interface (UI) 5 to the traveling direction determination part 24A. An operator may specify all tumor candidates or may specify some tumor candidates. For example, an operator may use the operating part 52 to specify the tumor candidates 810, 830, and 850 in that sequence.

(Traveling Direction Determination Part 24A)

The traveling direction determination part 24A receives the information (coordinate information) indicating the position of the specified tumor candidate and the information indicating the specified sequence. Subsequently, the traveling direction determination part 24A determines the traveling direction of the endoscopic probe 110 based on the specified sequence for the tumor candidates. When the tumor candidates have been specified by the operating part 52 in a sequence of the tumor candidates 810, 820, 830, 840, and 850, the traveling direction determination part 24A determines the direction (arrow Z1 direction) according to the sequence along the large intestine as the traveling direction of the endoscopic probe 110. Moreover, as another example, when the tumor candidates have been specified by the operating part 52 in a sequence of the tumor candidates 810, 830, and 850, the traveling direction determination part 24A determines the direction (arrow Z1 direction) according to the sequence along the large intestine as the traveling direction of the endoscopic probe 110.

On the other hand, when the tumor candidates have been specified by the operating part 52 in a sequence of the tumor candidates 850, 840, 830, 820, and 810, the traveling direction determination part 24A determines the direction (arrow Z2 direction) according to the sequence along the large intestine as the traveling direction of the endoscopic probe 110. The arrow Z2 direction is the direction opposite from the arrow Z1 direction.

In the example shown in FIG. 7, when the tumor candidate 810 side corresponds to the entry of the body cavity (the large intestine), the arrow Z1 direction corresponds to the direction in which the endoscopic probe 110 is advancing and the arrow Z2 direction corresponds to the direction in which the endoscopic probe 110 is retracting.

The traveling direction determination part 24A outputs the information indicating the traveling direction (advancing or retracting) of the endoscopic probe 110 to the decision part 25.

(Decision Part 25)

The decision part 25, as with the first embodiment, receives the position information indicating the position of the tip of the endoscopic probe 110 in the volume data indicating the large intestine and the direction information indicating the direction of the tip from the position matching part 23. Moreover, the decision part 25 receives the information indicating the traveling direction (advancing or retracting) of the endoscopic probe 110 from the traveling direction determination part 24A. Therefore, the decision part 25, as with the first embodiment, determines the position of a viewpoint and the view direction used for image generation processing based on the position of the tip, the direction of the tip, and the traveling direction of the endoscopic probe 110. In other words, the decision part 25 sets a position that is a predetermined distance (distance L1 or distance L2) away from the position of the tip of the endoscopic probe 110 in the traveling direction as the position of the viewpoint VP. Additionally, the decision part 25 sets the direction of the tip of the endoscopic probe 110 as a view direction used for image generation processing.

The image generation part 26, as was the case with the first embodiment, reads volume data from the storage part 3 and generates virtual endoscopic image data showing the internal portion of the large intestine according to the viewpoint and view direction decided by the decision part 25. The display-control part 4, as was the case with the first embodiment, displays the endoscopic image and virtual endoscopic image side by side on the display part 51. Alternatively, the display-control part 4 may superimpose the endoscopic image and virtual endoscopic image to display on the display part 51.

Based on the above, even when the traveling direction is identified based on the position of the tumor candidate identified by the CAD 27, it is possible to generate virtual endoscopic images, which correspond to the endoscopic image and which show the view in the traveling direction of the endoscopic probe 110, in a manner that is intuitively and easily understood for an operator.

(Measurement Part 28)

The measurement part 28 receives the position information indicating the position of the tumor candidate from the CAD 27 and obtains the distance from the reference point preset as a reference to each tumor candidate. The measurement part 28 outputs the information indicating the distance to each tumor candidate to the display-control part 4. For example, the measurement part 28 uses the tip portion of the endoscopic probe 110 as a reference point to obtain the distance from the tip portion to each tumor candidate. The display-control part 4 displays the information indicating the distance to the corresponding tumor candidate in the vicinity of each tumor candidate shown on the virtual endoscopic image. The measurement part 28 corresponds to an example of the "measurement part".

Figure 8A:
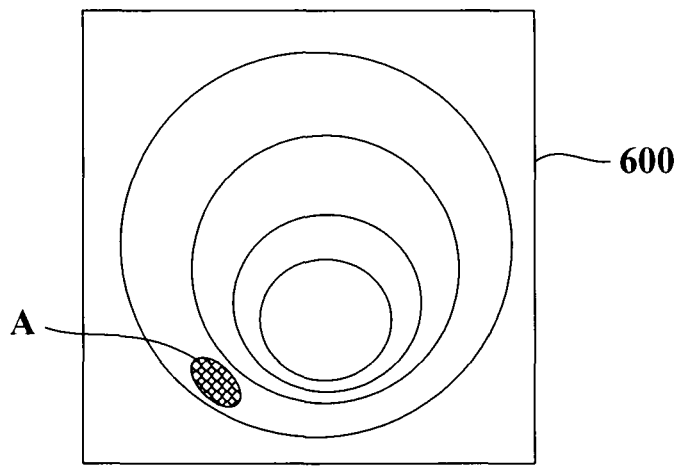
FIG. 8A is a diagram showing a state in which a marker indicating a tumor candidate is superimposed and displayed on a virtual endoscopic image.
Figure 8B:
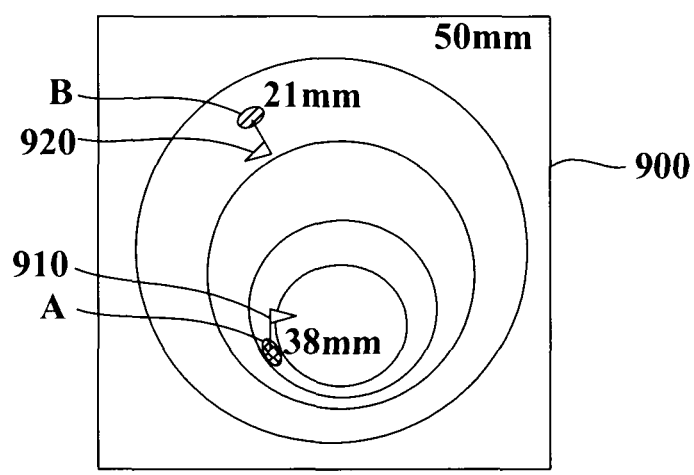
FIG. 8B is a diagram showing a state in which a marker indicating a tumor candidate is superimposed and displayed on a virtual endoscopic image.

FIG. 8A and FIG. 8B show a display example of the distance to a tumor candidate. FIG. 8A shows the endoscopic image 600 generated by the endoscopic probe 110. The tumor candidate A is shown on the endoscopic image 600. FIG. 8B shows the virtual endoscopic image 900 when the endoscopic probe 110 is retracted. The tumor candidate A and tumor candidate B are shown on the virtual endoscopic image 900. The display-control part 4 displays the information indicating the distance (38 mm) from the tip portion of the endoscopic probe 110 to the tumor candidate A in the vicinity of the tumor candidate A. Additionally, the display-control part 4 displays the information indicating the distance (21 mm) from the tip portion of the endoscopic probe 110 to the tumor candidate B in the vicinity of the tumor candidate B.

Based on the above, by displaying the distance to each tumor candidate, even when the viewpoint of the endoscopic image is different from the viewpoint of the virtual endoscopic image, it is possible for an operator to easily understand the anteroposterior relationship for each viewpoint.

In addition, the display-control part 4 may display the distance between the viewpoint of the endoscopic image and the viewpoint of the virtual endoscopic image on the display part 51. For example, the display-control part 4 may receive the information indicating a predetermined distance from the tip portion of the endoscopic probe 110 (distance L1 or distance L2) from the decision part 25 and may display the value of the distance L1 or distance L2 on the display part 51.

The view direction for generating the virtual endoscopic image is the same as the view direction on the endoscopic image. Therefore, tumor candidates which can be observed from the direction opposite from the view direction may be hid in the haustra of the large intestine and may not be displayed on the virtual endoscopic image. For example, even when the endoscopic probe 110 is retracted, the view direction for generating the virtual endoscopic image is the same as the view direction on the endoscopic image. In this case, tumor candidates which can be observed from the direction opposite from the view direction may be hid in the haustra of the large intestine and may not be displayed on the virtual endoscopic image. Hence, it is preferred to display the haustra on the virtual endoscopic image by making them translucent. Based on this, an operator can recognize the tumor candidates hid in the haustra. Alternatively, it is preferred to superimpose a recognizable marker on the position of the tumor candidate to display it.

When the haustra of the large intestine is displayed by making them translucent, the image generation part 26 identifies the haustra of the large intestine based on the pixel value (for example, CT value) of the volume data and generates the virtual endoscopic image data in a state in which the haustra is translucent. Subsequently, the display-control part 4 displays the virtual endoscopic image in a state in which the haustra is translucent on the display part 51. Based on this, an operator can recognize tumor candidates present at the backside of the haustra.

When superimposing a marker on the position of a tumor candidate, the display-control part 4 generates a marker indicating the tumor candidate. The display-control part 4 receives the position information indicating the position of the tumor candidate from the CAD 27, and then generates a marker indicating the tumor candidate.

The display-control part 4 superimposes a marker indicating the tumor candidate on the virtual endoscopic image to display on the display part 51.

For example, as shown in FIG. 8B, the display-control part 4 superimposes the marker 910 on the position of the tumor candidate A and superimposes the marker 920 on the position of the tumor candidate B to display on the display part 51. Based on this, even in the case in which the haustra are present in front of the tumor candidate, an operator can recognize the presence of tumor candidates by the marker.

The image processing part 2A and display-control part 4 may be composed of a processing system, which is not shown in the Figures, such as CPU, GPU, or ASIC and a storage system, which is not shown in the Figures, such as ROM, RAM, or HDD, respectively. In the storage system, an image processing program for executing the function of the image processing part 2A, and a display-control program for executing the function of the display-control part 4 are stored. Additionally, the image processing program includes a position detection program for executing the function of the position detection part 21, an extraction program for executing the function of the extraction part 22, a position matching program for executing the function of the position matching part 23, a traveling direction determination program for executing the function of the traveling direction determination part 24A, a decision program for executing the function of the decision part 25, an image generation program for executing the function of the image generation part 26, a program for executing the function of the CAD 27, and a measurement program for executing the function of the measurement part 28. Moreover, a processing system such as CPU executes each program stored in the storage system; thereby, the functions of each part are executed.

The medical image processing system 1 according to the first embodiment may have the function that the medical image processing system 1A according to the second embodiment provides. For example, the medical image processing system 1 according to the first embodiment may comprise the CAD 27 to specify tumor candidates and to perform processing using the tumor candidates. Additionally, the medical image processing system 1 according to the first embodiment may comprise the measurement part 28 to measure the distance from the position of the tip of the endoscopic probe 110 to each tumor candidate and to perform processing using the distance.

In the first embodiment and second embodiment, when the endoscopic probe 110 is advanced, the virtual endoscopic image data may be generated by setting the position of the tip portion 111 of the endoscopic probe 110 as the position of the viewpoint VP. Even in this case, when the endoscopic probe 110 is retracted, by generating the virtual endoscopic image data by setting the position that is the distance L2 away from the tip portion 111 in the backward direction as the position of the viewpoint VP, it is possible to operate the endoscopic probe 110 while confirming a region backward from the endoscopic image in advance. For example, when the traveling direction determination part 24 or the traveling direction determination part 24A determines that the endoscopic probe 110 is advancing, the decision part 25 decides a position of the tip portion 111 as the position of the viewpoint. On the other hand, when the traveling direction determination part 24 or the traveling direction determination part 24A determines that the endoscopic probe 110 is retracting, the decision part 25 decides a position that is the distance L2 away from the tip portion 111 in the traveling direction (retracting direction) as the viewpoint. Even in this case, it is possible to improve the efficiency of examination and to improve safety of operation of the endoscopic probe 110 when the endoscopic probe 110 is traveled backward (pulled back).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of embodiments described herein may be made without departing from the spirit of the inventions. The accompanying claims and their equivalents are intended to cover such forms or modifications as would fall within the scope and spirit of the inventions.

What is claimed is:

1. A medical image processing device comprising:
    a detection part that detects a position and a direction of an endoscope;
    a storage part that stores medical image data showing tubular tissues generated by a medical imaging device different from said endoscope;
    an image generation part that receives information indicating a traveling direction in which said endoscope is traveling within said tubular tissues and a speed of the endoscope and automatically generates, based on the received information indicating the traveling direction and speed, virtual endoscopic image data showing an internal portion of said tubular tissues based on said medical image data with a viewpoint, said viewpoint being one of the position of the endoscope and a position that is a predetermined distance away from the position of said endoscope in the traveling direction; and
    a display-control part that receives endoscopic image data showing the internal portion of said tubular tissues generated by said endoscope and that displays an endoscopic image based on said endoscopic image data and displays a virtual endoscopic image generated from the virtual endoscopic image data generated by the image generation part on a display.

2. The medical image processing device according to claim 1, wherein said image generation part generates said virtual endoscopic image data with the direction of said endoscope as a view direction.

3. The medical image processing device according to claim 1, further comprising:
    an identification part that identifies a tumor candidate based on said medical image data; and
    a determination part that receives a sequence of observations regarding said tumor candidate to determine said traveling direction of said endoscope based on said sequence.

4. The medical image processing device according to claim 3, further comprising a measurement part that obtains a distance from the position of said endoscope to said tumor candidate, wherein:
    said display-control part displays said distance on said display.

5. The medical image processing device according to claim 3, wherein:
    said display-control part generates a marker indicating said tumor candidate, superimposes said marker on a position of said tumor candidate in the virtual endoscopic image and displays the virtual endoscopic image on said display.

6. A method for processing a medical image, comprising:
    detecting a position and a direction of an endoscope;
    storing medical image data showing tubular tissues generated by a medical imaging device different from said endoscope;
    an image generation step of receiving information indicating a traveling direction in which said endoscope is traveling within said tubular tissues and a speed of the endoscope and automatically generating, based on the received information indicating the traveling direction and speed, virtual endoscopic image data showing an internal portion of said tubular tissues based on said medical image data having a viewpoint, said viewpoint being one of the position of the endoscope and a position that is a predetermined distance away from the position of said endoscope in the traveling direction; and
    a display-control step of receiving endoscopic image data showing the internal portion of said tubular tissues generated by said endoscope and for displaying an endoscopic image based on said endoscopic image data, and displaying a virtual endoscopic image generated from the virtual endoscopic image data, on a display.

7. The method for processing a medical image according to claim 6, wherein:
    said image generation step generates said virtual endoscopic image data with the direction of said endoscope as a view direction.

8. The method for processing a medical image according to claim 6, further comprising:
    identifying a tumor candidate based on said medical image data; and
    receiving a sequence of observations regarding said tumor candidate to determine said traveling direction of said endoscope based on said sequence.

9. The method for processing a medical image according to claim 8, further comprising obtaining a distance from the position of said endoscope to said tumor candidate, wherein:
    said display-control step displays said distance on said display.

10. The method for processing a medical image according to claim 8, wherein:
    said display-control step generates a marker indicating said tumor candidate, superimposes said marker on a position of said tumor candidate in the virtual endoscopic image, and displays the virtual endoscopic image on said display.

* * * * *